(12) United States Patent
Su et al.

(10) Patent No.: US 11,033,599 B2
(45) Date of Patent: Jun. 15, 2021

(54) *PENNISETUM* EXTRACT, PROCESS FOR MANUFACTURING THE SAME AND USES THEREOF (71) Applicant: METAL INDUSTRIES RESEARCH & DEVELOPMENT CENTRE, Kaohsiung (TW)

(72) Inventors: Ren-Wei Su, Kaohsiung (TW); Pei-Jung Lien, Kaohsiung (TW); Yu-Ren Huang, Kaohsiung (TW); Tz-Choung Chou, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 0 days.

(21) Appl. No.: 16/204,724

(22) Filed: Nov. 29, 2018

(65) Prior Publication Data

US 2019/0160135 A1    May 30, 2019

(30) Foreign Application Priority Data

Nov. 30, 2017 (TW) .................. 106141732

(51) Int. Cl.
*A61K 36/899*    (2006.01)
*A61P 19/10*    (2006.01)

(52) U.S. Cl.
CPC ............. *A61K 36/899* (2013.01); *A61P 19/10* (2018.01); *A61K 2236/13* (2013.01); *A61K 2236/15* (2013.01); *A61K 2236/17* (2013.01); *A61K 2236/333* (2013.01)

(58) Field of Classification Search
None
See application file for complete search history.

(56) References Cited

FOREIGN PATENT DOCUMENTS

TW    201336504 A    9/2013

OTHER PUBLICATIONS

Sunano, Procedure of brewing alcohol as a staple food: case study of the fermented cereal liquor "Parshot" as a staple food in Dirashe special woreda, southern Ethiopia, 2016, Food Science & Nutrition, 4: 544-554.*
Johari et al., Value Addition of Pearl Millet, 2015, Annals of Biology, 31: 291-293.*
Pearl Millet 2020 https://en.wikipedia.org/wiki/Pearl_millet.*
Pennisetum 2020 http://www.theplantlist.org/browse/A/Poaceae/Pennisetum/.*
Office Action dated Sep. 25, 2018 issued by Taiwan Intellectual Property Office for counterpart application No. 106141732.
Search Report dated Sep. 25, 2018 issued by Taiwan Intellectual Property Office for counterpart application No. 106141732.
English Abstract Translation of Search Report dated Sep. 25, 2018.
Office Action dated Feb. 19, 2019 issued by by Taiwan Intellectual Property Office for counterpart application No. 106141732.
Office Action dated May 26, 2020 issued by Taiwan Intellectual Property Office for counterpart application No. 106141732.
Search Report dated May 26, 2020 issued by Taiwan Intellectual Property Office for counterpart application No. 106141732.
English Abstract Translation of Search Report dated May 26, 2020.
APak. J. Bot., 45(6): 2095-2100.
J. Mater. Environ. Sci. 7 (4) (2016) 1347-1356.
English Abstract Translation of Foreign Reference TW 201336504A.
Kaddafi et al.: "Effect of peral millet extract versus aldendronate on mandibles and salivaryglands of rats subjected to cafeteria diet associated with corticosteroids" Kaddafi et al., J. Mater. Environ. Sci. 7 (4) (2016), Feb. 28, 2016, pp. 1347-1356.
Norhafizah Md Zain et al.: "Potential of Napier Grass (*Pennisetum purpureum*) Extracts As a Natural Herbicide " Norhafizah Md Zain et al., Pak. J. Bot, 45(6): 2013., Mar. 3, 2012, pp. 2095-2100.
Office Action dated Sep. 25, 2018 issued by Taiwan Intellectual Property Office for counterpart application 106141732.
English Translation of Search Report dated Sep. 25, 2018 issued by Taiwan Intellectual Property Office for counterpart application 106141732.
Search Report dated Sep. 25, 2018 issued by Taiwan Intellectual Property Office for counterpart application 106141732.

* cited by examiner

*Primary Examiner* — Terry A McKelvey
*Assistant Examiner* — Catheryne Chen
(74) *Attorney, Agent, or Firm* — WPAT, P.C., Intellectual Property Attorneys; Anthony King (57) ABSTRACT

The present disclosure provides a *Pennisetum* extract, process for manufacturing the same, and uses thereof for inhibiting differentiation and/or activation of osteoclast, and prevention and/or treatment of osteoporosis.

7 Claims, 6 Drawing Sheets

*PENNISETUM* EXTRACT, PROCESS FOR MANUFACTURING THE SAME AND USES THEREOF

BACKGROUND

1. Field of the Disclosure

The present disclosure relates to *Pennisetum* extract, process for manufacturing the same, and uses thereof for inhibiting differentiation and/or activation of osteoclast, and prevention and/or treatment of osteoporosis.

2. Description of the Related Art

Osteoporosis is currently the second most prevalent disease after cardiovascular disease. The World Health Organization defines osteoporosis as a systemic bone disease characterized by reduced bone mass and deterioration of microstructures of bone tissues, causing bone fragility and increased risk of fracture.

With the prevalence of osteoporosis, the global consumption of bone and joint health supplements has increased year by year, and is expected to reach $9.09 billion in market sales in 2017. However, products that use natural herbs as the main raw material are still rare in the market.

SUMMARY

The present disclosure provides an extract composition comprising a *Pennisetum* extract, which can be utilized for inhibiting differentiation and/or activation of osteoclast, and prevention and/or treatment of osteoporosis.

Hence, the present disclosure provides an extract composition comprising a *Pennisetum* extract, wherein the *Pennisetum* extract is manufactured by a process comprising following steps: (a) providing *Pennisetum*; and (b) extracting the *Pennisetum* with an alcohol solution to obtain a *Pennisetum* alcohol extract.

The present disclosure further provides a process for manufacturing the extract composition of claim 1, which comprises manufacturing the *Pennisetum* extract, and the process for manufacturing the *Pennisetum* extract comprises following steps: (a) providing *Pennisetum*; and (b) extracting the *Pennisetum* with an alcohol solution to obtain a *Pennisetum* alcohol extract.

The present disclosure further provides a A method for preventing and/or treating osteoporosis in a subject in need of such treatment, comprising administering to the subject an effective amount of an extract composition comprising a *Pennisetum* extract, wherein the *Pennisetum* extract is manufactured by a process comprising following steps: (a) providing *Pennisetum*; and (b) extracting the *Pennisetum* with an alcohol solution to obtain a *Pennisetum* alcohol extract.

DETAILED DESCRIPTION

The present disclosure provides an extract composition comprising a *Pennisetum* extract, wherein the *Pennisetum* extract is manufactured by a process comprising following steps: (a) providing *Pennisetum*; and (b) extracting the *Pennisetum* with an alcohol solution to obtain a *Pennisetum* alcohol extract.

The present disclosure further provides a process for manufacturing the extract composition of claim 1, which comprises manufacturing the *Pennisetum* extract, and the process for manufacturing the *Pennisetum* extract comprises following steps: (a) providing *Pennisetum*; and (b) extracting the *Pennisetum* with an alcohol solution to obtain a *Pennisetum* alcohol extract.

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the extract of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "prevention" as used herein refers to delaying the onset of symptoms in a susceptible individual, and reducing the occurrence of an illness or symptom, or inhibiting the occurrence of an illness or symptom, or arresting the development of an illness or symptom.

The term "treating" or "treatment" as used herein denotes reversing, alleviating, inhibiting the progress of, or improving the disorder, disease or condition to which such term applies, or one or more symptoms of such disorder, disease or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

The *Pennisetum* according to the present invention refers to *Poaceae Pennisetum*, preferably *Pennisetum purpureum* Schumach., 1827, which is also called elephant grass. It is a perennial grass species originating in South Africa and is one of the main forage crops in Taiwan. For example, the *Pennisetum* described in the present invention may be *Pennisetum purpureum* Schum. (CV.TLG1-7) developed by Taiwan Livestock Research Institute, Council of Agriculture, or a subsequently improved variety. *Pennisetum* has good productivity, environmental tolerance and excellent price competitiveness, and has the advantage of large-scale commercialization compared with traditional Chinese herbal medicine. More preferably, the *Pennisetum* of the present invention may be referred to the *Pennisetum purpureum* Schum., CV.TLG2, which has been approved by Taiwan Food and Drug Administration, Ministry of Health and Welfare as a raw material for food use. It can be used in the fields of food, biotechnology or medicine, and there is no doubt about safety.

The *Pennisetum* of the present invention is preferably a whole plant of *Pennisetum*, and the *Pennisetum* in the step (a) is preferably washed, dried and pulverized before extraction. For example, the sludge or the like adhered to the *Pennisetum* can be cleaned with water, and dried at a temperature of, for example, about 30° C. to about 70° C. for about 12 to about 48 hours, preferably dried at about 50° C. for about 24 hours until the water content is less than about 10%. Then, pulverization can be performed using, for example, a pulverizer to improve extraction efficiency.

In a preferred specific embodiment of the present invention, the *Pennisetum* is immersed in the alcohol solution for extraction, and more preferably, the *Pennisetum* is immersed in the alcohol solution and is subjected to ultrasonic vibration for extraction, for example, ultrasonic vibration for 1 to 12 hours. The ratio of the *Pennisetum* to the alcohol solution is not limited. In the preferred specific embodiment of the present invention, the ratio of the *Pennisetum* to the alcohol solution is about 1:1 to about 1:30; preferably, about 1:2 to about 1:20; and more preferably, about 1:3 to about 1:10.

In the step (b), the alcohol may be C1 to C7 alcohol, and may refer to linear or branched, substituted or unsubstituted, mono- or poly-functional, and saturated or unsaturated alcohol; preferably unsubstituted, mono-functional and saturated alcohol. Preferably, the alcohol is C1 to C4 alcohol. In one preferred embodiment of the present disclosure, the alcohol is selected from the group consisting of methanol, ethanol, n-propanol, isopropanol, n-butanol, iso-butanol, sec-butanol, tert-butanol, 1-pentanol, 2-pentanol, 3-pentanol, 2-methyl-1-butanol, 2-methyl-2-butanol, 3-methyl-2-butanol, 3-methyl-1-butanol, 2,2-dimethyl-1-propanol, 1-hexanol, 2,4-hexadiene-1-ol, 2-methyl-cyclopentanol, cyclohexanol, 1-heptanol, 2-heptanol, or cycloheptyl alcohol. The alcohol can be used solely or in combinations. More preferably, the alcohol is methanol or ethanol; most preferably, the alcohol is ethanol, such as an aqua solution containing 95% ethanol.

After extraction, a solid portion can be removed to obtain the *Pennisetum* alcohol extract. The manner of removing the solid portion is well known to those of ordinary skill in the art, for example, but not limited to, filtration, centrifugation, precipitation, and the like. In a preferred specific embodiment of the present invention, the extraction step (b) can be repeated, and the *Pennisetum* alcohol extracts are collected and combined.

Preferably, the process for manufacturing the *Pennisetum* extract of the present invention further comprises: (c) extracting the *Pennisetum* alcohol extract with ethyl acetate to obtain a *Pennisetum* ethyl acetate fraction. For example, the *Pennisetum* alcohol extract can be subjected to liquid-liquid extraction by using ethyl acetate. That is, the above step (c) may comprise: (c1) mixing the *Pennisetum* alcohol extract with a mixed solution of ethyl acetate and water to form a mixture; (c2) allowing the mixture to stand until phase separation of the ethyl acetate and the water; and (c3) collecting the ethyl acetate fraction.

In a preferred specific embodiment of the present invention, the mixed solution is provided with ethyl acetate and water in a volume ratio of about 1:5 to about 5:1, preferably in a volume ratio of about 1:3 to about 3:1, more preferably, in a volume ratio of about 1:1. The *Pennisetum* alcohol extract is thoroughly mixed in the mixed solution to form a mixture. The mixture is allowed to stand until phase separation of ethyl acetate and water, and the ethyl acetate portion is collected to obtain the *Pennisetum* ethyl acetate fraction. Similarly, the extraction step (c) can be repeated, for example, 3 to 10 times, and the *Pennisetum* ethyl acetate fractions are collected and combined.

Preferably, the method according to the present invention may further include concentrating and/or drying the *Pennisetum* extract. The methods of concentration and drying are well known to those of ordinary skill in the art, such as concentration under reduced pressure, natural air drying or freeze drying. Preferably, the *Pennisetum* alcohol extract and the *Pennisetum* ethyl acetate fraction are both concentrated to dryness under reduced pressure.

Figure 1:
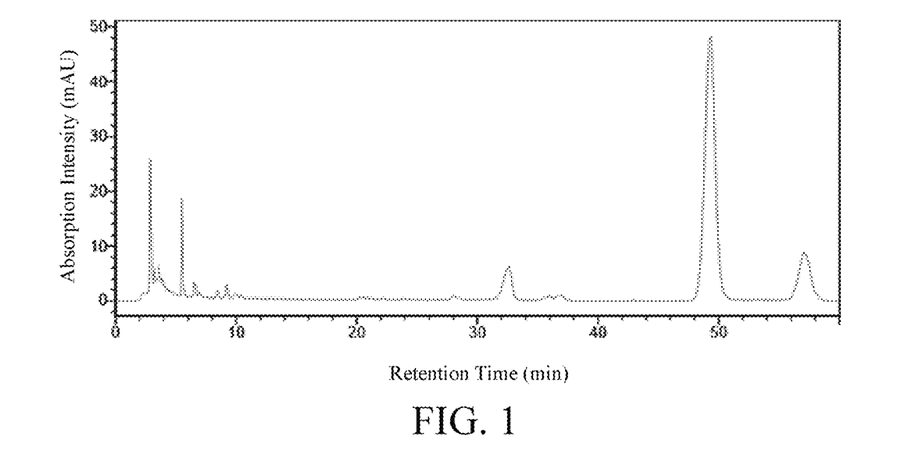
FIG. 1 shows a high-performance liquid chromatogram of a *Pennisetum* alcohol extract.
Figure 2:
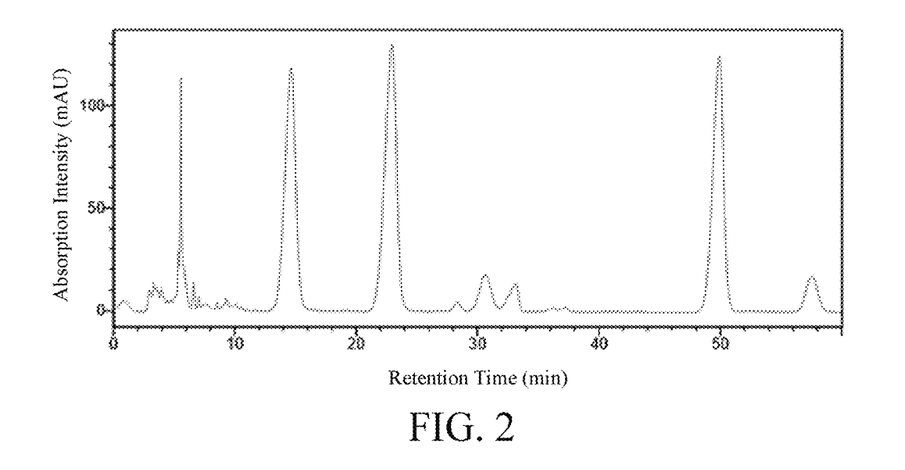
FIG. 2 shows a high-performance liquid chromatogram of a *Pennisetum* ethyl acetate fraction.

In a preferred specific embodiment of the present invention, the *Pennisetum* alcohol extract and the *Pennisetum* ethyl acetate fraction are respectively analyzed by the high-performance liquid chromatography (HPLC) to establish their HPLC chromatogram. The analysis conditions are as follows:

Column: Ultra C18 (5 μm×250 mm×4.6 mm)

Loading: solvent of methanol, sample concentration of 1000 ppm, injection volume of 20 μL Elution: mobile phase of methanol, flow rate of 1 mL/min Detection: detection wavelength of 400 nm The HPLC chromatogram of the *Pennisetum* alcohol extract and the *Pennisetum* ethyl acetate fraction are respectively shown in FIG. 1 and FIG. 2, and the retention time of the main peaks in each figure is shown in Table 1 below:

TABLE 1

Main peaks of retention time for *Pennisetum* alcohol extract (FIG. 1) and *Pennisetum* ethyl acetate fraction (FIG. 2)

| | Retention time (min) | | | | | | |
|---|---|---|---|---|---|---|---|
| | Peak 1 | Peak 2 | Peak 3 | Peak 4 | Peak 5 | Peak 6 | Peak 7 |
| FIG. 1 | 2.896 | 5.513 | 32.575 | 49.297 | 57.125 | — | — |
| FIG. 2 | 5.556 | 14.636 | 22.904 | 30.631 | 33.131 | 49.900 | 57.533 |

The extract composition according to the present disclosure is preferably a pharmaceutical composition or a food composition.

The pharmaceutical composition according to the present disclosure is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art.

The external route as used herein is also known as local administration, includes but is not limited to administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets or liposome or microencapsulation preparations.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution. The aerosol composition may optionally contain additional formulation excipients well known in the art such as surfactants e.g. oleic acid or lecithin and cosolvents e.g. ethanol Topical preparations may be administered by one or more applications per day to the affected area; over the skin areas occlusive dressings may advantageously be used. Continuous or prolonged delivery may be achieved by an adhesive reservoir system.

In the food composition of the present disclosure, the extract composition can be added to a conventional food composition (i.e. the edible food or drink or precursors thereof) in the manufacturing process of the food composition. Almost all food compositions can be supplemented with the extract composition of the present disclosure. The food compositions that can be supplemented with the extract composition of the present disclosure include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

The present disclosure further provides a use of the aforementioned extract composition for inhibiting differentiation and/or activation of osteoclast.

The present disclosure further provides a use of the aforementioned extract composition for prevention and/or treatment of osteoporosis.

The present disclosure further provides a method for inhibiting differentiation and/or activation of osteoclast, and for preventing and/or treating osteoporosis in a subject in need of such treatment, comprising administering to the subject an effective amount of the aforementioned extract composition optionally with a pharmaceutically acceptable carrier or excipient. That is, the extract composition of the present disclosure inhibits differentiation and/or activation of osteoclast in the subject, thus can be utilized for prevention and/or treatment of osteoporosis in the subject.

In a specific embodiment of the present invention, in the assay using a RAW 264.7 mouse macrophage cell line model, the co-culture with the *Pennisetum* extract can significantly inhibit the osteoclast differentiation and activation induced by RANKL, indicating that an extract composition containing the *Pennisetum* extract has the effect of preventing and treating osteoporosis.

In a preferred specific embodiment of the present invention, the use of the extract composition according to the present invention is for the preparation of a medicament for inhibiting the NFATc1 entering into the cell nucleus and inhibiting osteoclast differentiation.

The following examples are given for illustrating the method for manufacturing the composite fabric of the present disclosure, but are not intended to limit the scope of the present invention.

Example 1: Cytotoxicity Assay of *Pennisetum* Alcohol Extract

Preparation of *Pennisetum* alcohol extract: fresh *Pennisetum* was washed, dried and pulverized, and then extracted with a 95% aqueous solution of ethanol, wherein the volume ratio of the *Pennisetum* to the aqueous solution of ethanol was 1:3 to 1:10. The mixture was subjected to ultrasonic vibration, and the liquid portion was collected and concentrated under reduced pressure to obtain the *Pennisetum* alcohol extract.

Figure 3:
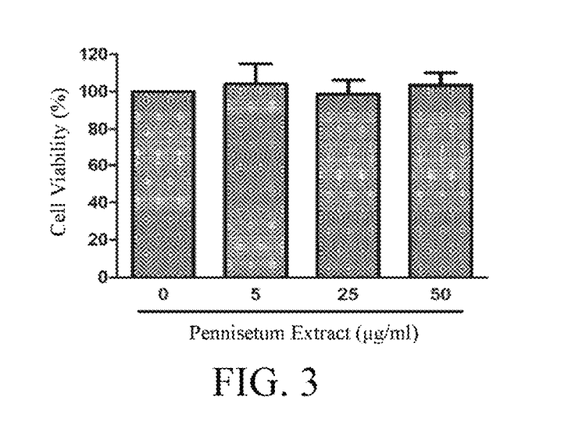
FIG. 3 shows results of the cytotoxicity assay of the *Pennisetum* alcohol extract.

RAW 264.7 mouse macrophages were subcultured in a DMEM medium (Dulbecco's modified Eagle medium) in 24-well plates ($5 \times 10^5$ cells/well) and respectively added with the *Pennisetum* alcohol extract (concentration: 5 µg/mL, 25 µg/mL, 50 µg/mL). After 24 hours of culture, the culture solution was replaced with an α-minimal essential medium (α-MEM) containing 0.5 mg/mL cell viability analytical reagent (MTT reagent). The cells were cultured at 37° C. for 2 to 3 hours. The supernatant of the culture solution was then removed by suction. Then, 200 µL DMSO was added to dissolve the cells, and an enzyme-linked immunosorbent assay reader (ELISA reader) was used to determine the cell viability by absorbance at a wavelength of 540 nm. A group in which no *Pennisetum* extract was added was used as the Control Group, and was set to viability of 100%. The results are shown in FIG. 3.

The above results show that none of the various concentrations of the *Pennisetum* alcohol extract significantly affected the cell viability, so that the *Pennisetum* alcohol extract is at least not cytotoxic at a concentration of 50 µg/mL or less.

Example 2: Assay for Inhibition of Osteoclast Differentiation by *Pennisetum* Alcohol Extract RAW 264.7 mouse macrophages were subcultured in a DMEM medium for 24 hours in 24-well plates ($5 \times 10^5$ cells/well). The culture solution was replaced with α-MEM, added with 10% fetal bovine serum (FBS), 100 ng/mL receptor activator of nuclear factor κ-B ligand (RANKL) and *Pennisetum* alcohol extract (the concentration is as shown in Table 2 below) and co-cultured for 5 days. The cells were then treated with 10% formalin for 10 minutes, and then stained with tartrate-resistant acid phosphatase (TRAP), as shown in FIG. 4A to FIG. 4E. The TRAP activity in the osteoclasts of the Control Group 2-2 and the Experimental Groups 2-1, 2-2 and 2-3 was also determined by setting the Control Group 2-2 as 100%, and the results are shown in FIG. 5. TRAP is one of the markers of the osteoclasts and can be used to determine the differentiation/activation state of the osteoclasts.

TABLE 2

Test conditions and results of inhibition to osteoclast differentiation/activation by *Pennisetum* alcohol extract

Figure 4A:
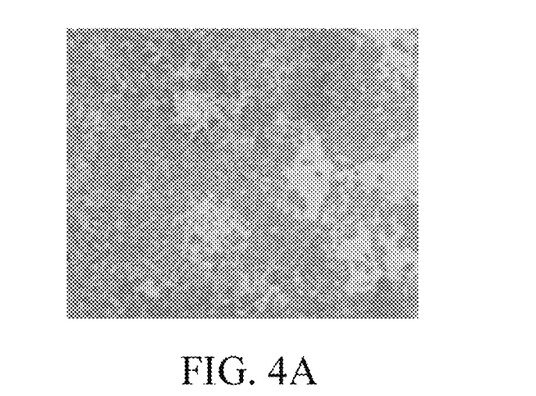
FIG. 4A, FIG. 4B, FIG. 4C, FIG. 4D and FIG. 4E show results of the assay for inhibition of osteoclast differentiation by the *Pennisetum* alcohol extract.
Figure 4B:
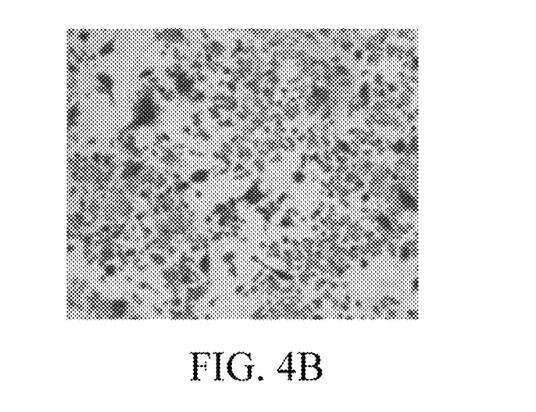
Figure 4C:
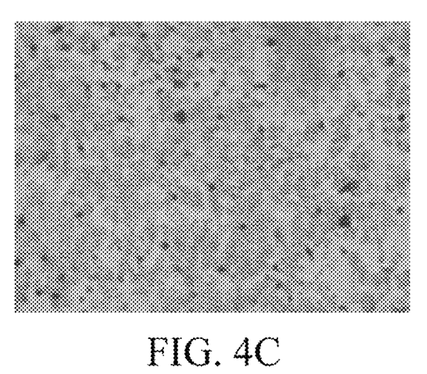
Figure 4D:
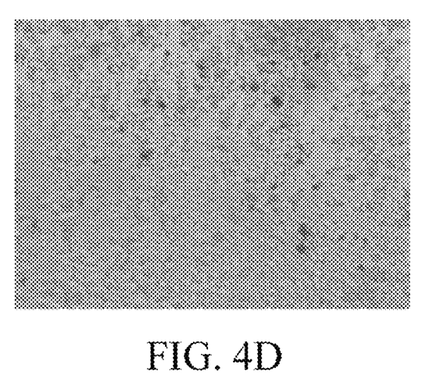
Figure 4E:
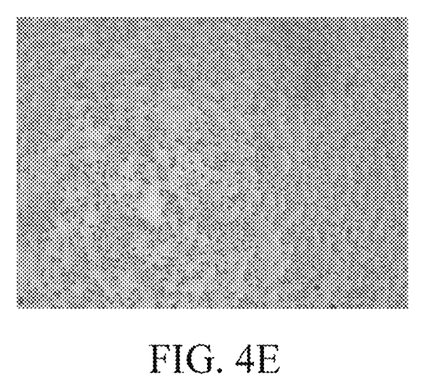
Figure 5:
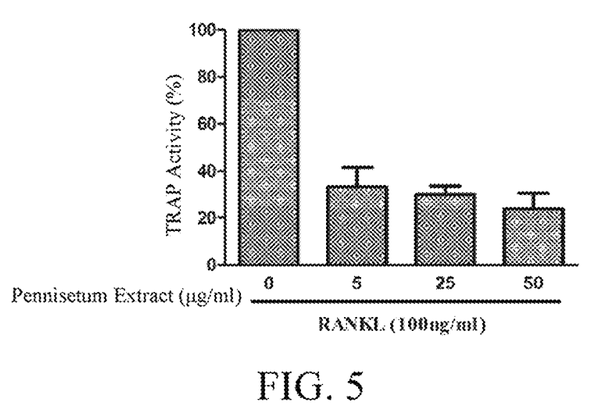
FIG. 5 shows results of the assay for inhibition of osteoclast activation by the *Pennisetum* alcohol extract.

| Group | RANKL | *Pennisetum* Alcohol Extract | Result |
|---|---|---|---|
| Control Group 2-1 | − | — | FIG. 4A |
| Control Group 2-2 | + | — | FIG. 4B |
| Experimental Group 2-1 | + | 5 µg/ml | FIG. 4C |
| Experimental Group 2-2 | + | 25 µg/ml | FIG. 4D |
| Experimental Group 2-3 | + | 50 µg/ml | FIG. 4E |

As can be seen from FIGS. 4A and 4B, RANKL can induce osteoclast differentiation and form a multinuclear feature. Referring to FIGS. 4C, 4D and 4E, it can be seen that the *Pennisetum* alcohol extract can inhibit osteoclast differentiation. In addition, as shown in FIG. 5, the *Pennisetum* alcohol extract can inhibit TRAP activity in osteoclasts. Hence, it shows that the *Pennisetum* alcohol extract can inhibit the osteoclast differentiation and/or activation in deed, and further can be used for preventing and/or treating osteoporosis.

Example 3: Assay for Inhibition of Osteoclast Differentiation by *Pennisetum* Ethyl Acetate Fraction Preparation of *Pennisetum* ethyl acetate fraction: the above-mentioned *Pennisetum* alcohol extract was taken and mixed with an ethyl acetate/water mixed solution having a volume ratio of 1:1, the mixture was allowed to stand until phase separation, and the ethyl acetate portion was collected and concentrated under reduced pressure to obtain the *Pennisetum* ethyl acetate fraction.

RAW 264.7 mouse macrophages were subcultured in a DMEM medium for 24 hours in 24-well plates ($5 \times 10^5$ cells/well). The culture solution was then replaced with α-MEM, added with 10% FBS, 100 ng/mL RANKL and/or 50 µg/mL *Pennisetum* ethyl acetate fraction (as shown in Table 3 below) and co-cultured for 5 days. Then, the cells were treated with 10% formalin for 10 minutes, and then stained with TRAP, as shown in FIG. 6A to FIG. 6C.

TABLE 3

Test conditions and results of inhibition to osteoclast differentiation/activation by *Pennisetum* ethyl acetate fraction

Figure 6A:
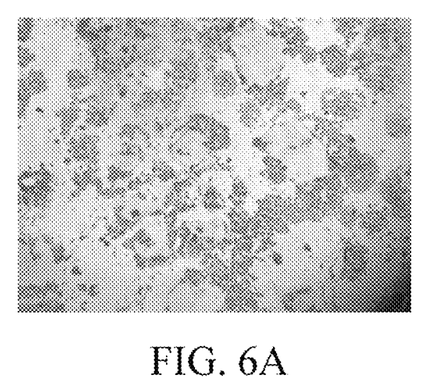
FIG. 6A, FIG. 6B and FIG. 6C show results of the assay for inhibition of osteoclast differentiation by the *Pennisetum* ethyl acetate fraction.
Figure 6B:
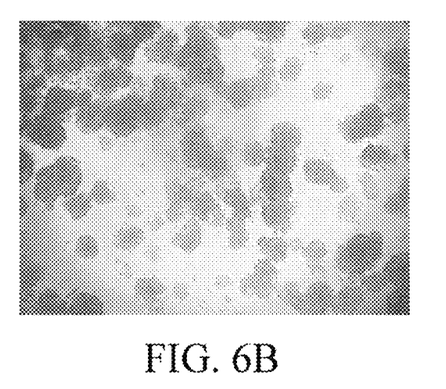
Figure 6C:
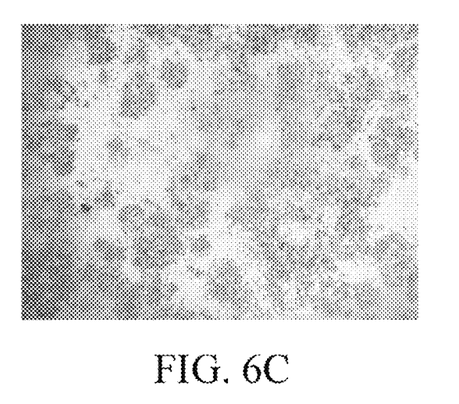
Figure 7A:
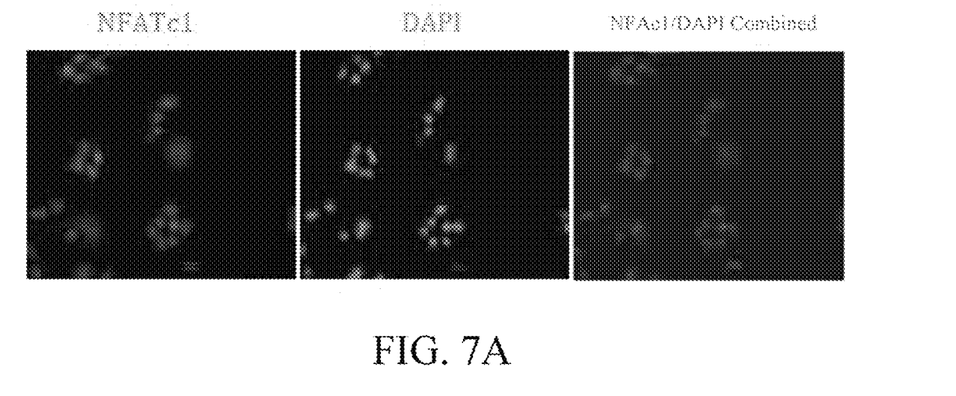
FIG. 7A, FIG. 7B and FIG. 7C show results of the assay for inhibition of NFATc1 entering into the cell nucleus by the *Pennisetum* ethyl acetate fraction.
Figure 7B:
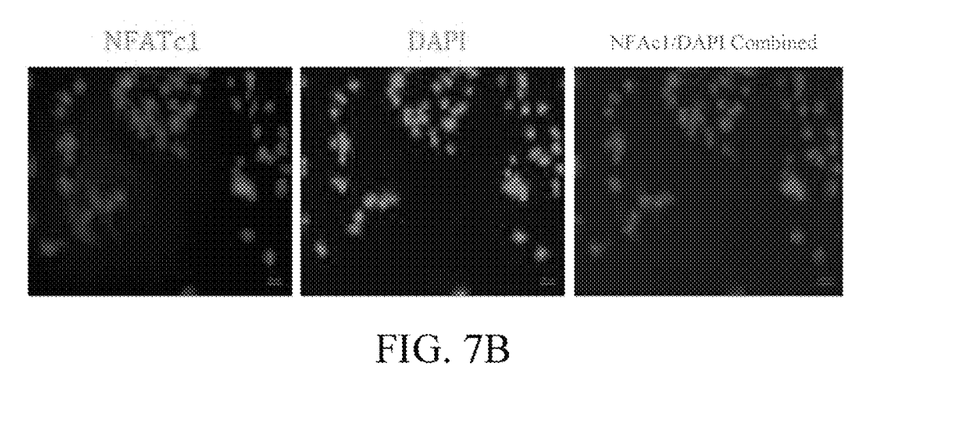
Figure 7C:
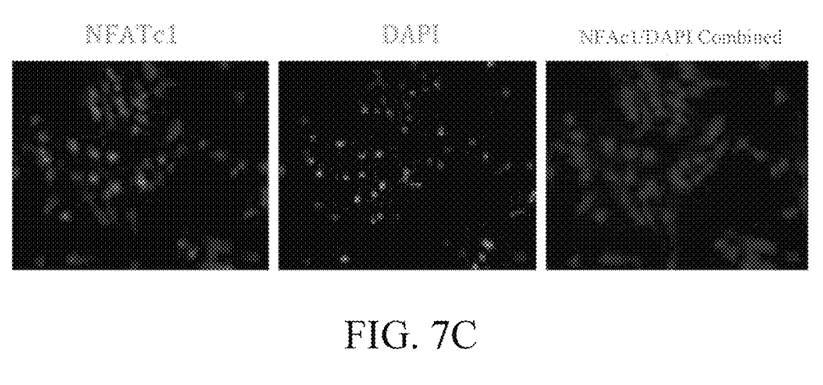

| Group | RANKL | Ethyl Acetate Fraction | Result |
|---|---|---|---|
| Control Group 3-1 | − | − | FIGS. 6A, 7A |
| Control Group 3-2 | + | − | FIGS. 6B, 7B |
| Experimental Group 3-1 | + | + | FIGS. 6C, 7C |

In addition, the Control Groups 3-1 and 3-2 and the Experimental Group 3-1 were stained with nuclear factor of activated T-cells, cytoplasmic 1 (NFATc1) and 4',6-diamidino-2-phenylindole (DAPI), and the results are shown in FIG. 7A to FIG. 7C respectively.

As can be seen from FIG. 6A to FIG. 6C, the *Pennisetum* ethyl acetate fraction can inhibit osteoclast differentiation and can be used for preventing and/or treating osteoporosis. In addition, as shown in FIG. 7A to FIG. 7C, the *Pennisetum* ethyl acetate fraction may inhibit osteoclast differentiation by inhibiting NFATc1 entering into the cell nucleus.

Example 4: Assay for Anti-Osteoporosis of *Pennisetum* Alcohol Extract

In this example, an in vivo assay for anti-osteoporosis activity of the *Pennisetum* extract was carried out on ovariectomized SD female rats in an animal feeding experiment mode, and the analysis of the femur bone mineral density and trabecular bone measurement was performed to confirm the pharmacological activity. The experimental method is as follows:

(1) Test substance and control substances: The test group (L) uses the *Pennisetum* alcohol extract prepared in the foregoing Example 1 as the test substance. The blank control group (Control) and the ovariectomized group (OVX) were administered with ethanol as the control substance. The positive control group (E2) was administered with estrogen as the control substance.

(2) Test animals: Test animals (including the test group, ovariectomized group and positive control group) were ovariectomized SD female rats, and the test on animals simulating the menopausal mode was started 2 weeks after oophorectomy. The blank control group was SD female rats without oophorectomy (only subjected to sham surgery).

(3) Animal feeding management: The feeding environment was temperature 20° C. to 25° C.; humidity 65% to 80%; and lighting time 12 hours (monitoring environment every day). During the acclimation and test period, every 4 female rats were housed in an autoclaved plastic rearing cage (46 cm×25 cm×20 cm). Drinking water was treated with a reverse osmosis pure water machine, and then charged in a high temperature autoclaved plastic bottle to give the test animals for free drinking.

(4) Acclimation: Ovariectomized SD female rats delivered by BioLASCO Co., Ltd. were acclimated for one week after entering the laboratory. During this period, clinical symptoms were observed every day, and healthy rats with normal weight gain were confirmed for the test.

(5) Administration of test substance and control substances: After one week of acclimation, the experimental rats were orally administered with different doses of *Pennisetum* alcohol extract, ethanol or estrogen for 3 consecutive months, and then all the experimental rats were fasted one night before sacrifice to simulate the clinically applicable route of administration for the human body. During the 3 consecutive months of testing, according to the weight of the day before the administration, the test group was administered with a solution of the *Pennisetum* alcohol extract (10 mL/kg), which was prepared by dissolving 50 mg of *Pennisetum* alcohol extract in 10.0 mL of 10% ethanol; the blank control group and the ovariectomized group were administered with 10% ethanol (10.0 mL/kg); and the positive control group was administered with estrogen, which was dissolved in 10% ethanol (10.0 mL/kg).

(6) The animal grouping was performed according to the body weight in an S-type order after the animals gained weight. The test substance and control substances administered to each group are shown in Table 4 below.

TABLE 4

Amount of test substances and control substances administered to each group

| Group | Administration Amount | Volume | Number of Mouse per Group |
|---|---|---|---|
| Control | 0.0 | 10.0 ml/kg | 6 |
| OVX | 0.0 | 10.0 ml/kg | 6 |
| E2 | estrogen 50 μg/kg | 1.0 ml/kg | 6 |
| L | 50 mg/kg | 10.0 ml/kg | 6 |

The bone density (mass/volume) of the appropriate bone was measured by a dual energy X-ray absorptiometer (DXA) or micro-computerized tomography (Micro-CT, μ-CT; also used to measure the trabecular number). During the measurement, the DXA with two different energies was used to scan the inspection site, then the X-rays passing through the tested site was received by a scintillation detector, and then a computer analyzed the data to calculate the bone quality of the tested site. The records of the percentage of bone mass (bone volume/tissue volume), trabecular separation/spacing (Tb.Sp), trabecular number (Tb.N) and bone mineral density (BMD) in each group are shown in Table 5.

It is represented by mean±standard error (S.E.M.) (n=6), and a, b, c, and d in the table represent statistical differences between the groups. The experimental data were statistically analyzed by one-way ANOVA. The statistical method of correlation index changes between the groups was statistically analyzed by Duncan test. However, since the physiological changes in the bone are extremely slow, if the significant difference between the groups according to the statistical analysis of bone mineral density and other indicators is $p<0.5$ (slightly significant), it is determined to have experimental significance.

TABLE 5

Digital medical image analysis of femurs of each group

| Group | Percentage of Bone Mass (%) | Trabecular Separation/ Spacing (mm) | Trabecular Number (1/mm) | Bone Mineral Density (mg/cm$^2$) |
|---|---|---|---|---|
| Control | 39.132 ± 3.782$^c$ | 0.227 ± 0.009$^a$ | 3.049 ± 0.162$^d$ | 0.640 ± 0.010$^c$ |
| OVX | 9.081 ± 1.359$^{ab}$ | 1.276 ± 0.127$^d$ | 0.794 ± 0.108$^{ab}$ | 0.617 ± 0.005$^a$ |
| E2 | 10.512 ± 1.071$^b$ | 1.103 ± 0.119$^c$ | 0.908 ± 0.085$^{bc}$ | 0.619 ± 0.001$^a$ |
| L | 10.941 ± 0.664$^b$ | 1.009 ± 0.061$^b$ | 0.972 ± 0.057$^c$ | 0.617 ± 0.006$^a$ |

(8) According to the digital medical image analysis of femurs, it was found that for the ovariectomized experimental animals, after the test group was fed for 90 consecutive days, the percentage of bone mass (10.941±0.664%) and the trabecular number (0.972±0.057/mm) were both significantly increased, and even higher than those of the positive control group (the percentage of bone mass was 10.512±1.071%; the trabecular number was 0.908±0.085/mm); and the analysis on the experimental data showed that when $p<0.5$, both the percentage of bone mass and the trabecular number had significant statistical differences from those of the ovariectomized group, and an effect of effectively delaying trabecular separation was realized. Hence, it can be seen that the *Pennisetum* alcohol extract of the present invention can achieve an anti-osteoporosis effect and can be used for the preparation of a medicament for preventing and/or treating osteoporosis.

While the present disclosure has been described and illustrated with reference to specific embodiments thereof, these descriptions and illustrations are not limiting. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. A method for preventing and/or treating osteoporosis in a subject in need of such treatment, comprising administering to the subject an effective amount of an extract composition comprising a *Pennisetum* extract, wherein the *Pennisetum* extract is manufactured by a process comprising following steps:
   (a) providing *Pennisetum*;
   (b) extracting the *Pennisetum* with an alcohol solution to obtain a *Pennisetum* alcohol extract; and
   (c) extracting the *Pennisetum* alcohol extract with ethyl acetate to obtain a *Pennisetum* ethyl acetate fraction.

2. The method of claim 1, wherein the extract composition further comprises a pharmaceutically acceptable carrier or excipient.

3. The method of claim 1, which is for inhibiting differentiation and/or activation of osteoclast.

4. The method of claim 1, which is for inhibiting the NFATc1 entering into the cell nucleus and inhibiting osteoclast differentiation.

5. The method of claim 1, wherein in the step (a), the *Pennisetum* is washed, dried and/or pulverized.

6. The method of claim 1, wherein the alcohol in the step (b) is C1 to C7 alcohol.

7. The method of claim 1, wherein the step (c) comprises:
   (c1) mixing the *Pennisetum* alcohol extract with a mixed solution of ethyl acetate and water to form a mixture;
   (c2) allowing the mixture to stand until phase separation of the ethyl acetate and the water; and
   (c3) collecting the ethyl acetate fraction.

* * * * *